US008903496B2

(12) United States Patent
Drees et al.

(10) Patent No.: US 8,903,496 B2
(45) Date of Patent: Dec. 2, 2014

(54) CLINICIAN PROGRAMMING SYSTEM AND METHOD

(75) Inventors: Scott Drees, Dallas, TX (US); Norbert Kaula, Arvada, CO (US); Yohannes Iyassu, Denver, CO (US); Scott G. Leyh, Cleveland Heights, OH (US); Richard J. Polefko, Parma, OH (US); Stephen C. Trier, Mayfield Heights, OH (US); Raymond L. Yoder, Willoughby, OH (US)

(73) Assignee: Greatbatch Ltd., Clarence, NY (US)

( * ) Notice: Subject to any disclaimer, the term of this patent is extended or adjusted under 35 U.S.C. 154(b) by 125 days.

(21) Appl. No.: 13/600,875

(22) Filed: Aug. 31, 2012

(65) Prior Publication Data

US 2014/0067012 A1 Mar. 6, 2014

(51) Int. Cl.
*A61N 1/372* (2006.01)
*A61N 1/08* (2006.01)
*G06F 3/14* (2006.01)
*G09G 5/00* (2006.01)

(52) U.S. Cl.
USPC ............... 607/59; 607/30; 345/156; 345/173

(58) Field of Classification Search
CPC ...................... A61N 1/37235; A61N 1/37247
USPC ..................................... 607/59, 30; 345/173
See application file for complete search history.

(56) References Cited

U.S. PATENT DOCUMENTS

| | | |
|---|---|---|
| 4,432,360 A | 2/1984 | Mumford et al. |
| 5,286,202 A | 2/1994 | De Gyarfas et al. |
| 5,304,206 A | 4/1994 | Baker, Jr. et al. |
| 5,312,446 A | 5/1994 | Holschbach et al. |
| 5,370,672 A | 12/1994 | Fowler et al. |
| 5,383,914 A | 1/1995 | O'Phelan |
| 5,421,830 A | 6/1995 | Epstein et al. |
| 5,628,776 A | 5/1997 | Paul et al. |
| 5,713,937 A | 2/1998 | Nappholz et al. |
| 5,722,999 A | 3/1998 | Snell |
| 5,724,996 A | 3/1998 | Piunti |
| 5,819,740 A | 10/1998 | Muhlenberg |

(Continued)

FOREIGN PATENT DOCUMENTS

| | | |
|---|---|---|
| EP | 1192972 | 4/2002 |
| EP | 2277586 | 1/2011 |

(Continued)

OTHER PUBLICATIONS

Extended European Search Report issued for Patent Application No. 13179897.7, dated Dec. 13, 2013, 6 pgs.

(Continued)

*Primary Examiner* — Allen Porter, Jr.
(74) *Attorney, Agent, or Firm* — Haynes and Boone, LLP

(57) ABSTRACT

A clinician programming system operable to control an implantable medical device includes a clinician programmer and a secondary unit. The clinician programmer has a housing, and includes a first display configured to display information indicative of the inputs by the clinician or display information indicative of status of an implantable pulse generator, the first display having a first display size. The secondary unit is separate from the housing of the clinician programmer and includes a secondary display. The secondary display is configured to communicate with the clinician programmer via the secondary display communication interface and configured to display information received via the secondary display communication interface.

41 Claims, 7 Drawing Sheets

(56) References Cited

U.S. PATENT DOCUMENTS

| | | |
|---|---|---|
| 5,879,374 A | 3/1999 | Powers et al. |
| 5,905,500 A | 5/1999 | Kamen et al. |
| 5,938,690 A | 8/1999 | Law et al. |
| 6,016,447 A | 1/2000 | Juran et al. |
| 6,016,448 A | 1/2000 | Busacker et al. |
| 6,052,624 A | 4/2000 | Mann |
| 6,083,156 A | 7/2000 | Lisiecki |
| 6,148,233 A | 11/2000 | Owen et al. |
| 6,154,675 A | 11/2000 | Juran et al. |
| 6,216,036 B1 | 4/2001 | Jenkins et al. |
| 6,246,414 B1 | 6/2001 | Kawasaki |
| 6,249,705 B1 | 6/2001 | Snell |
| 6,278,890 B1 | 8/2001 | Chassaing et al. |
| 6,307,554 B1 | 10/2001 | Arai et al. |
| 6,308,102 B1 | 10/2001 | Sieracki et al. |
| 6,325,756 B1 | 12/2001 | Webb et al. |
| 6,345,200 B1 | 2/2002 | Mouchawar et al. |
| 6,386,882 B1 | 5/2002 | Linberg |
| 6,442,432 B2 | 8/2002 | Lee |
| 6,525,727 B1 | 2/2003 | Junkins et al. |
| 6,564,104 B2 | 5/2003 | Nelson et al. |
| 6,587,104 B1 | 7/2003 | Hoppe |
| 6,611,267 B2 | 8/2003 | Migdal et al. |
| 6,622,048 B1 | 9/2003 | Mann et al. |
| 6,669,631 B2 | 12/2003 | Norris et al. |
| 6,786,405 B2 | 9/2004 | Weidenhoefer |
| 6,852,080 B2 | 2/2005 | Bardy |
| 6,882,982 B2 | 4/2005 | McMenimen et al. |
| 6,895,280 B2 | 5/2005 | Meadows et al. |
| 6,920,360 B2 | 7/2005 | Lee et al. |
| 6,931,155 B1 | 8/2005 | Gioia |
| 6,961,448 B2 | 11/2005 | Nichols et al. |
| 6,961,617 B1 | 11/2005 | Snell |
| 7,003,349 B1 | 2/2006 | Andersson et al. |
| 7,034,823 B2 | 4/2006 | Dunnet |
| 7,058,453 B2 | 6/2006 | Nelson et al. |
| 7,060,030 B2 | 6/2006 | Von Arx et al. |
| 7,065,409 B2 | 6/2006 | Mazar |
| 7,066,910 B2 | 6/2006 | Bauhahn et al. |
| 7,076,303 B2 | 7/2006 | Linberg |
| 7,087,015 B2 | 8/2006 | Comrie et al. |
| 7,092,761 B1 | 8/2006 | Cappa et al. |
| 7,107,102 B2 | 9/2006 | Daignault et al. |
| 7,142,923 B2 | 11/2006 | North et al. |
| 7,181,286 B2 | 2/2007 | Sieracki et al. |
| 7,181,505 B2 | 2/2007 | Haller et al. |
| 7,184,837 B2 | 2/2007 | Goetz |
| 7,239,926 B2 | 7/2007 | Goetz |
| 7,257,446 B2 | 8/2007 | Greenberg et al. |
| 7,266,412 B2 | 9/2007 | Stypulkowski |
| 7,299,085 B2 | 11/2007 | Bergelson et al. |
| 7,359,751 B1 | 4/2008 | Erickson et al. |
| 7,373,204 B2 | 5/2008 | Gelfand et al. |
| 7,440,806 B1 | 10/2008 | Whitehurst et al. |
| 7,452,336 B2 | 11/2008 | Thompson |
| 7,463,927 B1 | 12/2008 | Chaouat |
| 7,474,223 B2 | 1/2009 | Nycz et al. |
| 7,481,759 B2 | 1/2009 | Whitehurst et al. |
| 7,489,970 B2 | 2/2009 | Lee et al. |
| 7,496,403 B2 | 2/2009 | Cao et al. |
| 7,499,048 B2 | 3/2009 | Sieracki et al. |
| 7,505,815 B2 | 3/2009 | Lee et al. |
| 7,551,960 B2 | 6/2009 | Forsberg et al. |
| 7,602,384 B2 | 10/2009 | Rosenberg et al. |
| 7,617,002 B2 | 11/2009 | Goetz |
| 7,627,372 B2 | 12/2009 | Vaisnys et al. |
| 7,640,059 B2 | 12/2009 | Forsberg et al. |
| 7,657,317 B2 | 2/2010 | Thacker et al. |
| 7,685,005 B2 | 3/2010 | Riff et al. |
| 7,711,603 B2 | 5/2010 | Vanker et al. |
| 7,720,549 B2 | 5/2010 | Schroeppel et al. |
| 7,747,330 B2 | 6/2010 | Nolan et al. |
| 7,774,067 B2 | 8/2010 | Keacher et al. |
| 7,778,710 B2 | 8/2010 | Propato |
| 7,801,596 B2 | 9/2010 | Fischell et al. |
| 7,801,611 B2 | 9/2010 | Persen et al. |
| 7,805,199 B2 | 9/2010 | KenKnight et al. |
| 7,822,483 B2 | 10/2010 | Stone et al. |
| 7,853,323 B2 | 12/2010 | Goetz |
| 7,885,712 B2 | 2/2011 | Goetz et al. |
| 7,890,180 B2 | 2/2011 | Quiles et al. |
| 7,928,995 B2 | 4/2011 | Daignault |
| 7,934,508 B2 | 5/2011 | Behm |
| 7,940,933 B2 | 5/2011 | Corndorf |
| 7,953,492 B2 | 5/2011 | Corndorf |
| 7,953,612 B1 | 5/2011 | Palmese et al. |
| 7,957,808 B2 | 6/2011 | Dawant et al. |
| 7,978,062 B2 | 7/2011 | LaLonde et al. |
| 7,991,482 B2 | 8/2011 | Bradley |
| 8,014,863 B2 | 9/2011 | Zhang et al. |
| 8,021,298 B2 | 9/2011 | Barid et al. |
| 8,027,726 B2 | 9/2011 | Ternes |
| 8,046,241 B1 | 10/2011 | Dodson |
| 8,060,216 B2 | 11/2011 | Greenberg et al. |
| 8,068,915 B2 | 11/2011 | Lee et al. |
| 8,068,918 B2 | 11/2011 | Vallapureddy et al. |
| 8,078,440 B2 | 12/2011 | Otto et al. |
| 8,082,162 B2 | 12/2011 | Flood |
| 8,121,702 B2 | 2/2012 | King |
| 8,135,566 B2 | 3/2012 | Marshall et al. |
| 8,140,160 B2 | 3/2012 | Pless et al. |
| 8,140,167 B2 | 3/2012 | Donders et al. |
| 8,160,328 B2 | 4/2012 | Goetz et al. |
| 8,160,704 B2 | 4/2012 | Freeberg |
| 8,165,385 B2 | 4/2012 | Reeves et al. |
| 8,187,015 B2 | 5/2012 | Boyd et al. |
| 8,200,324 B2 | 6/2012 | Shen et al. |
| 8,200,340 B2 | 6/2012 | Skelton et al. |
| 8,219,206 B2 | 7/2012 | Skelton et al. |
| 8,233,991 B2 | 7/2012 | Woods et al. |
| 8,246,680 B2 | 8/2012 | Betz et al. |
| 8,249,713 B2 | 8/2012 | Fang et al. |
| 8,255,060 B2 | 8/2012 | Goetz et al. |
| 8,323,218 B2 | 12/2012 | Davis et al. |
| 8,326,433 B2 | 12/2012 | Blum et al. |
| 8,340,775 B1 | 12/2012 | Cullen et al. |
| 8,382,666 B1 | 2/2013 | Mao et al. |
| 8,386,032 B2 | 2/2013 | Bachinski et al. |
| 8,401,666 B2 | 3/2013 | Skelton et al. |
| 8,428,727 B2 | 4/2013 | Bolea et al. |
| 2001/0037220 A1 | 11/2001 | Merry et al. |
| 2003/0076301 A1 | 4/2003 | Tsuk et al. |
| 2003/0107572 A1 | 6/2003 | Smith et al. |
| 2003/0139652 A1 | 7/2003 | Kang et al. |
| 2003/0171911 A1 | 9/2003 | Fairweather |
| 2003/0177031 A1 | 9/2003 | Malek |
| 2003/0233129 A1* | 12/2003 | Matos ............................... 607/5 |
| 2004/0088374 A1 | 5/2004 | Webb et al. |
| 2004/0122477 A1 | 6/2004 | Whitehurst et al. |
| 2004/0210273 A1 | 10/2004 | Wang |
| 2005/0107831 A1 | 5/2005 | Hill et al. |
| 2005/0149356 A1 | 7/2005 | Cyr et al. |
| 2005/0168460 A1 | 8/2005 | Razdan et al. |
| 2005/0277872 A1 | 12/2005 | Colby et al. |
| 2006/0089888 A1 | 4/2006 | Roger |
| 2006/0095092 A1* | 5/2006 | Drew ............................... 607/60 |
| 2006/0100832 A1 | 5/2006 | Bowman |
| 2006/0241720 A1 | 10/2006 | Woods et al. |
| 2006/0242159 A1 | 10/2006 | Bishop et al. |
| 2006/0282168 A1 | 12/2006 | Sherman et al. |
| 2007/0043585 A1* | 2/2007 | Matos ............................... 705/1 |
| 2007/0078404 A1* | 4/2007 | Talarico et al. ................ 606/205 |
| 2007/0078497 A1 | 4/2007 | Vandanacker |
| 2007/0093998 A1 | 4/2007 | El-Baroudi et al. |
| 2007/0179349 A1 | 8/2007 | Hoyme et al. |
| 2007/0203537 A1 | 8/2007 | Goetz et al. |
| 2007/0203538 A1 | 8/2007 | Stone et al. |
| 2007/0203543 A1 | 8/2007 | Stone et al. |
| 2007/0213790 A1 | 9/2007 | Nolan et al. |
| 2008/0004675 A1 | 1/2008 | King et al. |
| 2008/0033303 A1 | 2/2008 | Wariar et al. |
| 2008/0046036 A1 | 2/2008 | King et al. |
| 2008/0140161 A1 | 6/2008 | Goetz et al. |
| 2008/0177362 A1 | 7/2008 | Phillips et al. |

(56) References Cited

U.S. PATENT DOCUMENTS

| | | |
|---|---|---|
| 2008/0218517 A1 | 9/2008 | Holmdahl |
| 2008/0262565 A1 | 10/2008 | Bentwich |
| 2008/0300659 A1* | 12/2008 | Matos .................. 607/60 |
| 2009/0018617 A1 | 1/2009 | Skelton et al. |
| 2009/0018619 A1 | 1/2009 | Skelton et al. |
| 2009/0024178 A1 | 1/2009 | Hennig |
| 2009/0048871 A1 | 2/2009 | Skomra |
| 2009/0089034 A1 | 4/2009 | Penney et al. |
| 2009/0099624 A1 | 4/2009 | Kokones et al. |
| 2009/0132009 A1 | 5/2009 | Torgenson |
| 2009/0136094 A1 | 5/2009 | Driver et al. |
| 2009/0196471 A1 | 8/2009 | Goetz et al. |
| 2009/0234873 A1 | 9/2009 | Li et al. |
| 2009/0264967 A1 | 10/2009 | Giftakis et al. |
| 2009/0281596 A1 | 11/2009 | King et al. |
| 2010/0004033 A1 | 1/2010 | Choe et al. |
| 2010/0010566 A1 | 1/2010 | Thacker et al. |
| 2010/0010574 A1 | 1/2010 | Skelton et al. |
| 2010/0010580 A1 | 1/2010 | Skelton et al. |
| 2010/0058462 A1 | 3/2010 | Chow |
| 2010/0076534 A1 | 3/2010 | Mock |
| 2010/0090004 A1 | 4/2010 | Sands et al. |
| 2010/0106475 A1 | 4/2010 | Smith et al. |
| 2010/0123547 A1 | 5/2010 | Stevenson et al. |
| 2010/0152534 A1 | 6/2010 | Kim et al. |
| 2010/0161345 A1 | 6/2010 | Cain et al. |
| 2010/0198103 A1 | 8/2010 | Meadows et al. |
| 2010/0198304 A1 | 8/2010 | Wang |
| 2010/0222845 A1 | 9/2010 | Goetz |
| 2010/0223020 A1 | 9/2010 | Goetz |
| 2010/0265072 A1 | 10/2010 | Goetz et al. |
| 2010/0268304 A1 | 10/2010 | Matos |
| 2010/0280417 A1* | 11/2010 | Skelton et al. .............. 600/595 |
| 2010/0280578 A1 | 11/2010 | Skelton et al. |
| 2011/0004059 A1 | 1/2011 | Arneson et al. |
| 2011/0015514 A1 | 1/2011 | Skalli et al. |
| 2011/0015693 A1 | 1/2011 | Williamson |
| 2011/0023343 A1 | 2/2011 | Turner et al. |
| 2011/0038498 A1 | 2/2011 | Edgar |
| 2011/0040546 A1 | 2/2011 | Gerber et al. |
| 2011/0040547 A1 | 2/2011 | Gerber et al. |
| 2011/0046697 A1 | 2/2011 | Gerber et al. |
| 2011/0054560 A1 | 3/2011 | Rosenberg et al. |
| 2011/0054870 A1 | 3/2011 | Dariush et al. |
| 2011/0077459 A1 | 3/2011 | Rofougaran |
| 2011/0077616 A1 | 3/2011 | Bennet et al. |
| 2011/0093030 A1 | 4/2011 | Goetz et al. |
| 2011/0093047 A1 | 4/2011 | Davis et al. |
| 2011/0093051 A1 | 4/2011 | Davis et al. |
| 2011/0153341 A1 | 6/2011 | Diaz-Cortes |
| 2011/0170739 A1 | 7/2011 | Gillam et al. |
| 2011/0172564 A1 | 7/2011 | Drew |
| 2011/0172737 A1 | 7/2011 | Davis et al. |
| 2011/0172744 A1 | 7/2011 | Davis et al. |
| 2011/0185178 A1 | 7/2011 | Gotthardt |
| 2011/0191275 A1 | 8/2011 | Lujan et al. |
| 2011/0224523 A1 | 9/2011 | Burdiman |
| 2011/0224665 A1 | 9/2011 | Crosby et al. |
| 2011/0246219 A1 | 10/2011 | Smith et al. |
| 2011/0264165 A1 | 10/2011 | Molnar et al. |
| 2011/0270358 A1 | 11/2011 | Davis et al. |
| 2011/0282414 A1 | 11/2011 | Kothandaraman et al. |
| 2011/0305376 A1 | 12/2011 | Neff |
| 2011/0307284 A1 | 12/2011 | Thompson et al. |
| 2011/0313268 A1 | 12/2011 | Kokones et al. |
| 2011/0313487 A1 | 12/2011 | Kokones et al. |
| 2012/0041518 A1 | 2/2012 | Kim et al. |
| 2012/0046715 A1 | 2/2012 | Moffitt et al. |
| 2012/0071947 A1 | 3/2012 | Gupta et al. |
| 2012/0083857 A1 | 4/2012 | Bradley et al. |
| 2012/0084689 A1 | 4/2012 | Ledet et al. |
| 2012/0089008 A1 | 4/2012 | Strehl et al. |
| 2012/0109230 A1 | 5/2012 | Kothandaraman et al. |
| 2012/0182244 A1* | 7/2012 | Arthur .................. 345/173 |
| 2012/0192874 A1 | 8/2012 | Bolea et al. |
| 2012/0215277 A1* | 8/2012 | Berg et al. ................ 607/32 |
| 2012/0215284 A1 | 8/2012 | Berg et al. |
| 2012/0239116 A1 | 9/2012 | Lee et al. |
| 2012/0256857 A1 | 10/2012 | Mak |
| 2012/0265269 A1 | 10/2012 | Lui et al. |
| 2012/0277828 A1 | 11/2012 | O'Connor et al. |
| 2012/0290041 A1 | 11/2012 | Kim et al. |
| 2012/0290272 A1 | 11/2012 | Bryan |
| 2012/0290976 A1 | 11/2012 | Lahm et al. |
| 2012/0296392 A1 | 11/2012 | Lee et al. |
| 2012/0296396 A1 | 11/2012 | Moffitt et al. |
| 2012/0296397 A1 | 11/2012 | Vansickle |
| 2012/0303087 A1 | 11/2012 | Moffitt et al. |
| 2012/0310300 A1 | 12/2012 | Kaula et al. |
| 2013/0023950 A1 | 1/2013 | Gauthier |
| 2013/0060299 A1 | 3/2013 | Polefko et al. |
| 2013/0060300 A1 | 3/2013 | Polefko et al. |
| 2013/0060301 A1 | 3/2013 | Polefko et al. |
| 2013/0060302 A1 | 3/2013 | Polefko et al. |
| 2013/0079848 A1 | 3/2013 | Campbell et al. |

FOREIGN PATENT DOCUMENTS

| | | |
|---|---|---|
| WO | WO 9959106 | 11/1999 |
| WO | WO 0209808 | 2/2002 |
| WO | WO 02084637 | 10/2002 |
| WO | WO 2009113102 | 9/2009 |
| WO | WO 2011028261 | 3/2011 |
| WO | WO 2011063248 | 5/2011 |
| WO | WO 2011104028 | 9/2011 |
| WO | WO 2011123669 | 10/2011 |
| WO | WO 2012018851 | 2/2012 |
| WO | WO 2012021862 | 2/2012 |
| WO | WO 2012135949 | 10/2012 |
| WO | WO 2013023085 | 2/2013 |

OTHER PUBLICATIONS

Synalink Features, SynaMed Web Page, http://synamed.com/synalinkFeatures.html., Copyright 2010, 2 pgs.

Boston Scientific Corporation, "Boston Scientific Precision Spectra System Programming Manual", Copyright 2010, 580 pgs.

* cited by examiner

CLINICIAN PROGRAMMING SYSTEM AND METHOD

FIELD OF THE INVENTION

This disclosure is directed to an external monitor connection for a clinician programmer.

BACKGROUND

Neurostimulation devices deliver therapy in the form of electrical stimulation pulses to treat symptoms and conditions, such as chronic pain, Parkinson's disease, or epilepsy, for example. Implantable neurostimulation devices, for example, deliver neurostimulation therapy via leads that include electrodes located proximate to the muscles and nerves of a patient.

Clinician programmers are used to control and program the neurostimulation devices with stimulation sequences to treat symptoms and conditions. These clinician programmers and devices of their type are relatively small to allow for easy transportation and storage. The portability has its price, however. It is difficult for more than one person to view the relatively small screen of a handheld programmer. People would have to crowd around the device to be able to attempt to see what is happening on the screen.

Further, even though the clinician programmer is portable, there are some areas where its use may be restricted. For instance, a clinician programmer may be covered under the drapes while a sales representative is talking to the patient. The clinician programmer thus may not be visible to the physician. As another example, the clinician programmer may not be a sterile device and cannot be taken into the sterile field in an operating room. Since the clinician programmer must remain outside of the sterile field, the physician is unable to read the screen while performing the procedure. Accordingly, the physician must verbally interact with and rely on someone (an external operator), who acts as his eyes and hands controlling the programmer outside of the sterile field. The situation could also be reversed, where the physician is doing the programming, and the staff is observing his/her actions, for example, talking to the patient at the head end of the surgery table. In any case, requiring an extra person results in additional time for the procedure to be completed as a result of the verbal communication of the programming device state and adjustments to be made between the physician and the external operator. The verbal interchange may also result in miscommunication which will add additional time to complete the procedure and possibly result in more severe consequences.

The present disclosure is directed to devices, systems, and methods that address one or more deficiencies in the prior art.

SUMMARY

This disclosure is directed to a patient programmer in communication with an external monitor that helps to alleviate the problems set out above. When demonstrating the device, for example, the screen can be displayed on a large monitor for group viewing. In addition, when used for a procedure within an operating room, the programmer can be kept outside the sterile field, but its user interface can be made available for viewing by the physician and others through a projector or large screen monitor. In many cases, the external screen may be the only screen that the physician can see, because the clinician programmer is under the cover or tucked away.

In one exemplary aspect, the present disclosure is directed to a clinician programming system operable to control an implantable medical device. The clinician programming system includes a clinician programmer with a housing. The clinician programmer includes: a processor and memory having executable instructions enabling programming of an implantable pulse generator; a user interface configured to receive inputs by a clinician instructing operation of an implantable pulse generator; a first display configured to display information indicative of the inputs by the clinician or display information indicative of status of an implantable pulse generator, the first display having a first display size; an implant communication interface configured to transmit information from the clinician programmer to an implantable pulse generator and configured to receive information from an implantable pulse generator; and a display communication interface configured to transmit content shown on the display. The clinician programming system also includes a secondary unit separate from the housing of the clinician programmer, the secondary unit having a secondary display of a second display size, the secondary display being configured to communicate with the clinician programmer via the secondary display communication interface and configured to display information received via the secondary display communication interface. The secondary display may display information either mirrored or extended from the clinician programmer.

In one exemplary aspect, the present disclosure is directed to a clinician programmer. The clinician programmer includes a first display configured to display information to a user relating to an implantable device; a user input mechanism configured to receive inputs from the user controlling content shown on the first display; a secondary unit communication interface selectively attachable to a secondary unit, the secondary unit communication interface configured to transmit information to a secondary unit having a secondary display and configured to receive information for processing from the secondary unit; and a controller configured to receive a user input from the user input mechanism, the user input selecting a first mode that sends a display signal to the secondary display causing content shown on the secondary display to mirror or extend content shown on the first display and a second mode that sends a display signal to the secondary display causing content shown on the secondary display to differ from content shown on the primary display.

In one exemplary aspect, the present disclosure is directed to a clinician programmer. The clinician programmer includes a programming software module configured to generate a treatment program executable on an implantable medical device as a result of a user input; an implant communication interface configured to send the treatment program to an implantable medical device to operate the implantable device and configured to receive information from the implantable device; a primary display configured to display information relating to the treatment program; a secondary display unit communication interface configured to transmit information to a secondary display unit and configured to receive information from a secondary display unit; a microphone in communication with the secondary display unit communication interface and configured to capture audio from the user for transmission from the secondary display unit communication interface; and a speaker in communication with the a secondary display unit communication interface and configured to receive signals representing audio captured at the secondary display unit.

In one exemplary aspect, the present disclosure is directed to a surgical arrangement used when programming an implantable medical device. The surgical arrangement includes: a non-sterile (or wrapped sterile) clinician programmer having a memory storing instructional information for programming an implantable pulse generator and having a first display screen configured to display the instructional information to a user, the clinician programmer having a secondary display unit interface comprising a transmitter and a receiver configured to send display signals and configured to receive instructional signals; a secondary unit comprising a second display screen sized larger than the clinician programmer first display screen, the second display screen being disposed for viewing from a sterile room and connectable with the clinician programmer, the secondary unit being configured to receive the instructional information from the clinician programmer and display the instructional information on the second display screen under the instruction of the clinician programmer; and an implantable pulse generator in communication with one of the secondary unit and the clinician programmer, the implantable pulse generator having a memory and processor configured to activate electrodes based on information received from said one of the secondary unit and the clinician programmer, the implantable pulse generator being configured to electrically receive said information displayed relating to an electrode of the implantable pulse generator.

In one exemplary aspect, the present disclosure is directed to a method for performing trial stimulation during neurostimulator implant surgery. The method includes: providing a clinician programmer having a first display screen having a first display screen size; providing an external secondary unit having a second display screen having a second display screen size that is visible to medical personnel, for example operating room staff working within the sterile field; providing at least one stimulation lead operable to provide electrical stimulation to target tissue within a patient; connecting the clinician programmer to the external monitor; operating the clinician programmer to control the stimulation provided through the stimulation lead and to display information related to the stimulation on the external monitor; and displaying information relating to the stimulation lead on either one of the first and the second display screens, or both.

In one exemplary aspect, the present disclosure is directed to a method for programming an implantable device. The method includes: receiving an input at a user interface on a tablet-style clinician programmer; generating a first display signal on the clinician programmer that updates content on a first display based on the received user input, the first display having a first size; generating a second display signal for transmission to a secondary unit having a second display separate from the clinician programmer, the second display having a second size, wherein generating the second display signal includes enhancing the content of the second display signal to provide a clear image on the second size display; and transmitting the second display signal from the clinician programmer to the second display.

BRIEF DESCRIPTION OF THE DRAWINGS

Aspects of the present disclosure are best understood from the following detailed description when read with the accompanying figures.

DETAILED DESCRIPTION

Figure 1B:
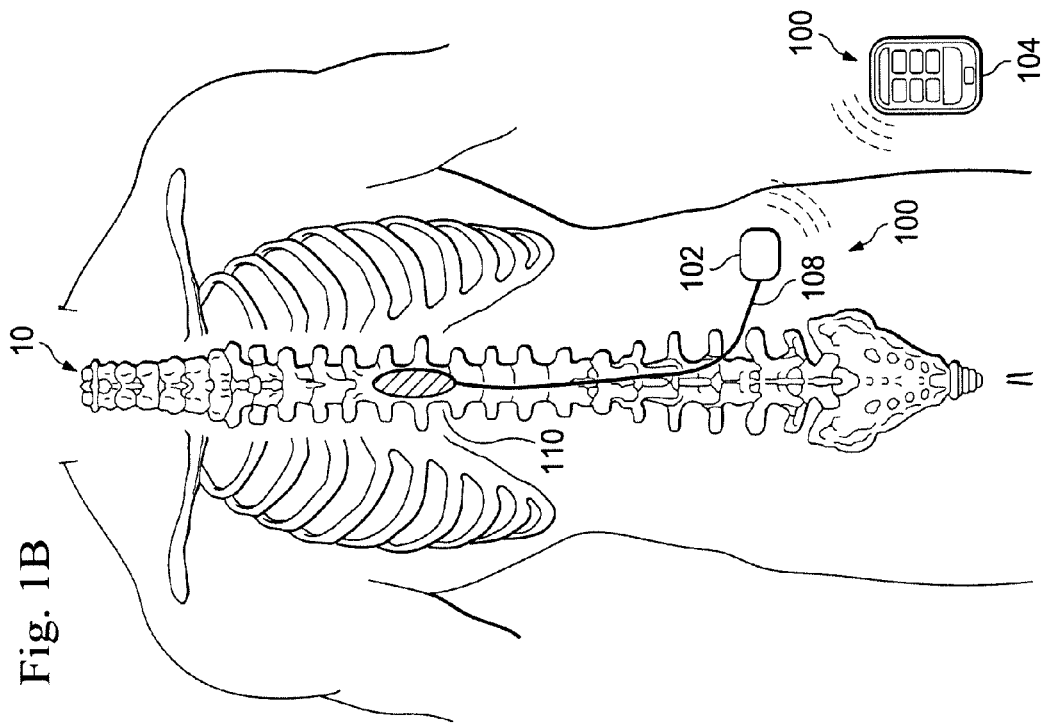
FIGS. 1A and 1B are illustrations of a patient's spine with an exemplary electrical stimulator treatment system disposed to treat a particular region of the spine in accordance with one aspect of the present disclosure.

The following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The devices, systems, and methods described herein introduce an improved way for controlling and programming an implanted medical device. They use a clinician programmer ("CP") with a first display electrically coupled (for example, coupled in a wired or wireless manner) to a second display disposed for viewing by others than the clinician performing the programming. In one example, the CP may be outside a sterile field, but may be in communication with a display viewable to others who are within the sterile field. This may be particularly helpful to surgeons who perform surgeries and must issue instructions to a programming clinician to direct or control an implant in a certain manner. The surgeon may look at the second display and see the settings and programming as it occurs on the CP, instead of relying merely on verbal feedback from the programming clinician. This may streamline the surgery and since the surgeon can now see the clinician programming screen, may help assure the surgeon that his instructions are being carried out as requested without relying solely on verbal feedback. This may reduce verbal communication errors between staff during programming. Accordingly, this may provide a level of redundancy and risk management not achieved when programming is performed with only a CP outside the sterile field. In another example, the CP sends information shown on its display to the second larger display for viewing by additional people. This may be particularly helpful during training processes, when the clinician may be instructing trainees or other clinicians in treatment techniques, for example.

Figure 1A:
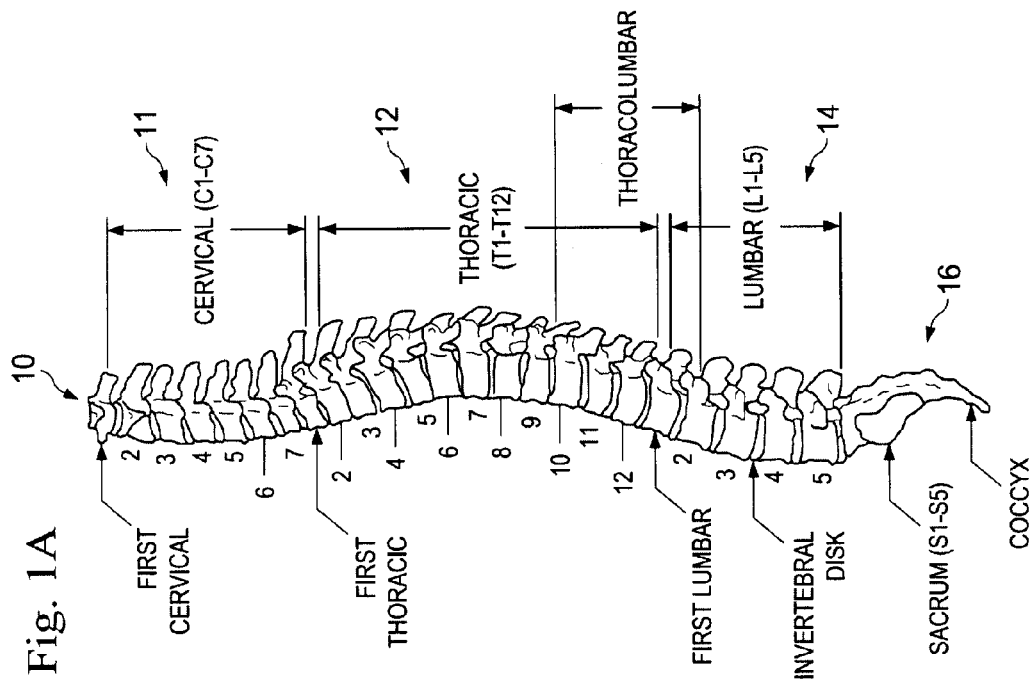

FIG. 1A is a side view of a spine 10, and FIG. 1B is a posterior view of the spine 10. FIG. 1B shows an exemplary electrical stimulator treatment system 100 disposed to treat a spinal region for treating a symptom, such as chronic pain. The system includes an implantable pulse generator (IPG) 102 that delivers electrical stimulation therapy to the patient, and a CP 104.

Referring now to FIGS. 1A and 1B, the spine 10 includes a cervical region 11, a thoracic region 12, a lumbar region 14, and a sacrococcygeal region 16. The cervical region 11 includes the top seven vertebrae, which may be designated with C1-C7. The thoracic region 12 includes the next twelve vertebrae below the cervical region 11, which may be designated with T1-T12. The lumbar region 14 includes the final five "true" vertebrae, which may be designated with L1-L5. The sacrococcygeal region 16 includes nine fused vertebrae that make up the sacrum and the coccyx. The fused vertebrae of the sacrum may be designated with S1-S5.

Neural tissue (not illustrated for the sake of simplicity) branches off from the spinal cord through spaces between the adjacent vertebrae. The neural tissue, along with the cord itself, can be individually and selectively stimulated in accordance with various aspects of the present disclosure. For example, referring to FIG. 1B, the IPG 102 is implanted inside the body. A conductive lead 108 is electrically coupled to the circuitry inside the IPG 102. The conductive lead 108 may be removably coupled to the IPG 102 through a connector, for example. A distal end of the conductive lead 108 is attached to one or more electrodes 110. In the example shown, the electrodes 110 are implanted adjacent to a desired nerve tissue in the thoracic region 12. The distal end of the lead 108 with its accompanying electrodes may be positioned beneath the dura mater using well-established and known techniques in the art.

The electrodes 110 deliver current drawn from the IPG 102, thereby generating an electric field near the neural tissue. The electric field stimulates the neural tissue to accomplish its intended functions. For example, the neural stimulation may alleviate pain in an embodiment. In other embodiments, a stimulator as described above may be placed in different locations throughout the body and may be programmed to address a variety of problems, including for example but without limitation; prevention or reduction of epileptic seizures, bladder control, weight control or regulation of heart beats.

It is understood that the IPG 102, the lead 108, and the electrodes 110 may be implanted completely inside the body, or may have only one or more components implanted within the body while other components remain outside the body. When they are implanted inside the body, the implant location may be adjusted (e.g., anywhere along the spine 10) to deliver the intended therapeutic effects of spinal cord electrical stimulation in a desired region of the spine. The IPG 102 in this system is a fully implantable, battery-powered neurostimulation device for providing electrical stimulation to a body region of a patient. In some embodiments, an external pulse generator (EPG) is used. The EPG is identical to the IPG but the connection is done through percutaneous wires (communication may still be wireless though). In the example shown in FIG. 1B, the IPG 102 is configured to provide neural stimulation to the spine. However, in other embodiments, IPG 102 may be a different type of pulse generator, including, for example, a pacemaker, a defibrillator, a trial stimulator or any other type of medical device. Here, the IPG 102 is structurally configured and arranged for wireless programming and control through the skin of the patient. Accordingly, it includes a transmitter and receiver capable of communicating with external programming and control devices, such as the CP 104. It also includes a rechargeable power source, such as a battery configured to be wirelessly recharged through the patient's skin when a charger is externally placed in the proximity of the IPG 102.

The CP 104 is typically maintained in a health care provider's possession and can be used to program the IPG 102 as a part of the implantation treatment and later during office visits. For example only, the CP 104 can define the available stimulation programs for the IPG 102 by enabling and disabling particular stimulation programs, can define the actual stimulation programs by creating defined relationships between pulses, and perform other functions.

Figure 2:
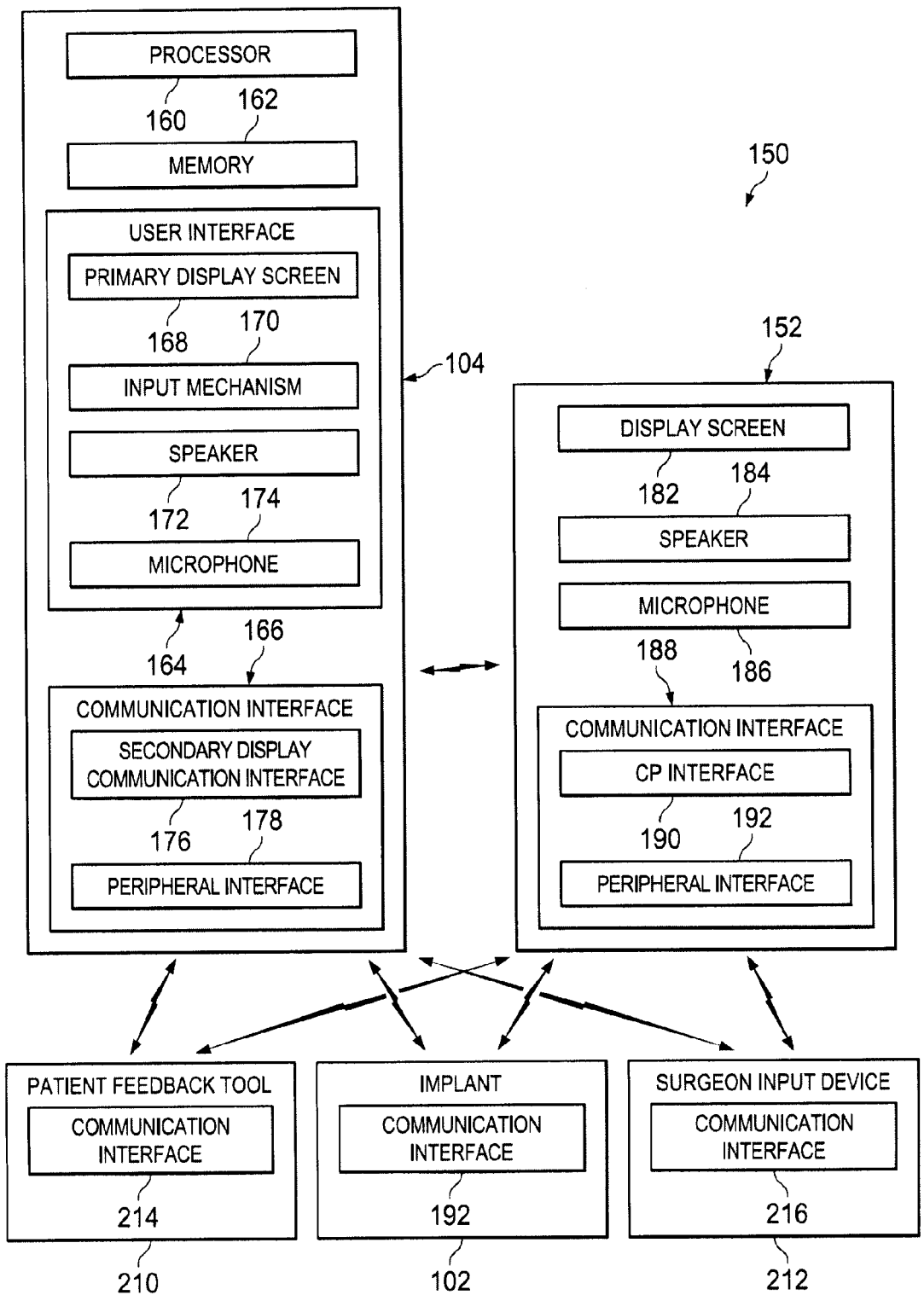
FIG. 2 is a block diagram showing an exemplary external monitor interface system in accordance with one aspect of the present disclosure.

FIG. 2 is a block diagram showing an exemplary clinician programming system 150. The programming system 150 includes the CP 104, the IPG 102, a secondary display unit 152, a patient feedback tool ("PFT") 210, and a surgeon input device 212.

The CP 104 is, in one embodiment, a tablet-style device with a touch screen and radios for communicating with active implantable medical devices, such as neurostimulators like the IPG 102. As can be seen in FIG. 2, the CP 104 includes a processor 160, memory 162, a user interface 164, and a communication interface 166.

As shown in FIG. 2, the user interface 164 includes a primary display screen 168, an input mechanism 170, a speaker 172, and a microphone 174. The speaker 172 and the microphone 174 enable audio communication between the CP 104 and the secondary display unit 152. For example, the speaker 172 may be linked with a microphone 186 on the secondary display unit 152, and the microphone 174 may enable communication with a speaker 184 on the secondary display unit 152. As described below, this may be useful when the CP 104 and the secondary display unit 152 are in different locations.

The communication interface 166 enables the CP 104 to communicate with other components of the clinician programming system 150. In the embodiment shown, the communication interface 166 includes a secondary display communication interface 176 and a peripheral interface 178. These, along with other elements of the CP 104, are described in detail with reference to FIG. 3.

Figure 3:
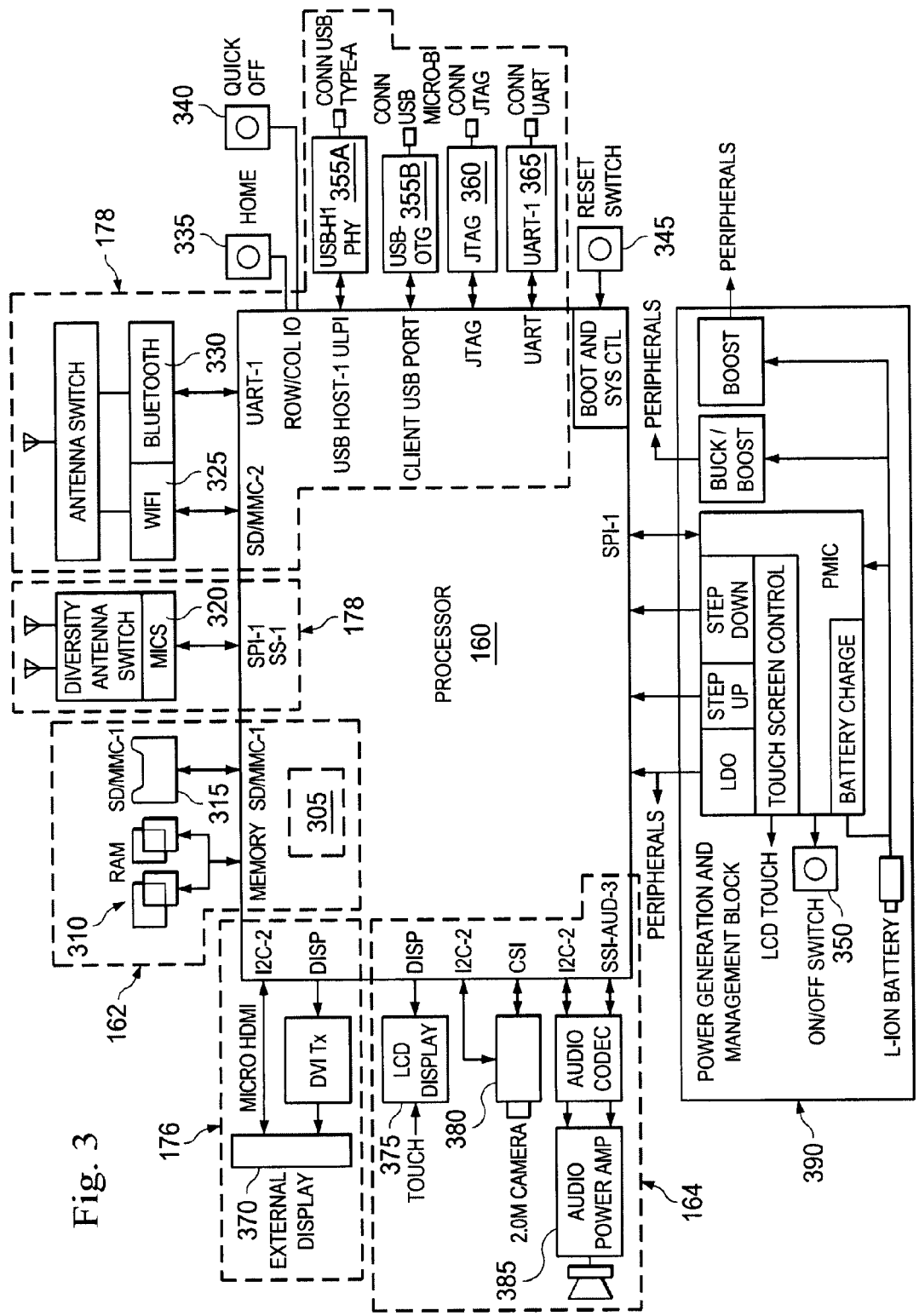
FIG. 3 is a block diagram of a clinician programmer for use in the exemplary external monitor interface system of FIG. 2.

FIG. 3 shows a block diagram of a more detailed construction of the CP 104. Referring to FIG. 3, the CP 104 includes a printed circuit board ("PCB") that is populated with a plurality of electrical and electronic components that provide power, operational control, and protection to the CP 104. The processor 160 is a controller for controlling the CP 104, and indirectly programming, controlling, and responding to the IPG 102, the secondary display unit 152, the PFT 210, and the surgeon input device 212. In one construction, the processor 160 is an applications processor model i.MX515 available from Freescale Semiconductor. More specifically, the i.MX515 applications processor has internal instruction and data caches, multimedia capabilities, external memory interfacing, and interfacing flexibility. Further information regarding the i.MX515 applications processor can be found in, for example, the "IMX51CEC, Rev. 4" data sheet; dated August 2010; published by Freescale Semiconductor at www.freescale.com, the content of the data sheet being incorporated herein by reference. Of course, other processing units, such as other microprocessors, microcontrollers, digital signal processors, etc., can be used in place of the processor 160.

The CP 104 includes memory 162, which can be internal to the processor 160 (e.g., memory 305), external to the processor 160 (e.g., memory 310), or a combination of both. The memory 162 stores sets of instructional information with stimulation control parameters that are available to be selected for delivery through the communication interface 166 to the IPG 102 for electrical stimulation therapy or to the secondary display unit 152 for display to a plurality of individuals in the surgical area or elsewhere. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 160 executes software that is capable of being stored in the RAM (e.g., during execution), the ROM (e.g., on a generally permanent basis), or another non-transitory computer readable medium such as another memory or a disc. The CP 104 also includes input/output ("I/O") systems that include routines for transferring information between components within the processor 160 and other components of the CP 104 or external to the CP 104.

Software included in the implementation of the CP 104 is stored in the memory 305 of the processor 160, RAM 310, ROM 315, or external to the CP 104. The software includes, for example, firmware, one or more applications, program data, one or more program modules, and other executable instructions. The processor 160 is configured to retrieve from memory and execute, among other things, instructions related to the control processes and methods described below for the CP 104. For example, the processor 160 is configured to execute instructions retrieved from the memory 162 for establishing a protocol to control the IPG 102. Some embodiments include software modules configured to provide instructions for accomplishing particular tasks handled by the CP 104. For example, the CP 104 includes a programming software module configured to generate a treatment or stimulation program based on input received from a user of the CP 104. A secondary display software module controls the signals and communication sent from the CP 104 to the secondary display unit 152. Additional exemplary software will be described in further detail below.

Since the secondary display screen 182 is larger than the primary display screen 164 as described below, the secondary display software module may be configured to enhance the resolution or otherwise format or modify the display signal in a way that creates a clearer image of the content on the secondary display. This may ensure that a relatively clear image is shown on a secondary screen having a larger screen size than that of the CP primary display screen 164, while not requiring as high resolution for the smaller primary display screen 164.

One memory shown in FIG. 3 is memory 310, which can be a double data rate (DDR2) synchronous dynamic random access memory (SDRAM) for storing data relating to and captured during the operation of the CP 104. In addition, a secure digital (SD) multimedia card (MMC) can be coupled to the CP for transferring data from the CP to the memory card via slot 315. Of course, other types of data storage devices can be used in place of the data storage devices shown in FIG. 3.

The peripheral interface 178 is configured, depending on the embodiment, to receive data or signals from the IPG 102, the PFT 210, and the surgeon input device 212. Accordingly, it may include an implant communication interface, a PFT communication interface, and a surgeon input device communication interface. The implant communication interface includes structure and components enabling the CP 104 to send or receive information to and from the IPG 102. For example, it may comprise a radio transceiver that enables one-way or two-way communication with the IPG 102. The interface 178 may include components for wireless or wired communication and may be configured with any of the components discussed above with reference to the secondary display communication interface 176. In one example, the implant communication interface 178 comprises a medical implant communication service (MICS) RF transceiver used to communicate with the IPG 102 to communicate desired changes and to receive status updates from and relating to the IPG 102, such as battery status and any error information. In this example, the MICS RF transceiver utilizes a loop antenna for the communications with the IPG 102. Other antennas, such as, for example, dipole, chip antennas, or other antennas known in the art also may be used. The CP 104 may also include a programming interface used during manufacturing to load an operating system and program the CP 104.

The PFT communication interface and the surgeon input device communication interface may include structure and components enabling the CP to send and receive information to and from the PFT and the surgeon input device. These interfaces may be similar to that of the implant communication interface, or alternatively, may be otherwise enabled. Depending on the embodiment, the PFT communication interface and the surgeon input device communication interface may be one or more ports for wired communication, such as universal serial bus (USB) connectivity 355, including a Type A port and a Micro-B port; a related port for supporting Joint Test Action Group (JTAG) or other plug-in style port, or may be wireless using, for example, Wi-Fi portion 325 and Bluetooth portion 330 that respectively include a Wi-Fi communication interface, a Bluetooth communication interface, an antenna switch, and a related antenna all of which allows wireless communication following the Wi-Fi Alliance standard and Bluetooth Special Interest Group standard. Of course, other wireless local area network (WLAN) standards and wireless personal area networks (WPAN) standards can be used with the CP 104. Any other interface enabling communication between the CP 104 and the PFT 120 or surgeon input device 212 may be used. In some embodiments, the interface 178 is the same as the interface 176.

The secondary display communication interface 176 includes multiple bi-directional radio communication capabilities. Specific wireless portions included with the CP 104 are a Wi-Fi bi-direction radio communication portion 325, and a Bluetooth bi-direction radio communication portion 330. The Wi-Fi portion 325 and Bluetooth portion 330 include a Wi-Fi communication interface, a Bluetooth communication interface, an antenna switch, and a related antenna all of which allows wireless communication following the Wi-Fi Alliance standard and Bluetooth Special Interest Group standard. Of course, other wireless local area network (WLAN) standards and wireless personal area networks (WPAN) standards can be used with the CP 104.

The CP 104 includes multiple communication portions for wired communication. Exemplary circuitry and ports for receiving a wired connector include a port for supporting universal serial bus (USB) connectivity 355, including a Type A port and a Micro-B port, a portion and related port for supporting Joint Test Action Group (JTAG) connectivity 360, and a portion and related port for supporting universal asynchronous receiver/transmitter (UART) connectivity 365. Of course, other wired communication standards and connectivity can be used with or in place of the types shown in FIG. 3.

The secondary display communication interface 176 includes the structure and components enabling the CP 104 to send or receive information to and from the secondary display unit 152. In one embodiment, the secondary display communication interface 176 is integral with the CP 104 and is available along an edge, such as a lower edge, under a protective cover of the CP 104. In one embodiment, the secondary display communication interface 176 includes a HDMI port formed in a housing of the CP 104. The interface 176 may allow connection to the external secondary display unit 152 via a micro High-Definition Multimedia Interface (HDMI) 370, which provides a compact audio/video interface for transmitting uncompressed digital data to the external display unit 152. The use of the HDMI connection 370 allows the CP 104 to transmit video (and audio) communication to the external display unit 152. This may be beneficial in situations where others (e.g., the surgeon) may want to view the information being viewed by a CP user. The surgeon typically has no visual access to the CP 104 in the operating room. The HDMI connection 370 allows the surgeon to view information from the CP 104, thereby allowing greater communication between the clinician and the surgeon. For a specific example, the HDMI connection 370 can broadcast a high definition television signal that allows the surgeon to view the same information that is shown on the LCD (discussed below) of the CP 104. In addition, as HDMI signals are compatible with DVI, the CP 104 can also be connected, with the proper cabling, to other external display devices that only support DVI input. In some embodiments, audio and video can be played independently. In other embodiments, audio and video can be played in a synchronized manner.

In another embodiment, the secondary display communication interface 176 includes a wireless transmitter and receiver configured to wirelessly communicate with the secondary display communication interface 176. In one example, it includes structure and encoding for Wi-Fi communication. In another example, it includes structure and encoding for Bluetooth communication. Additional wireless protocols are contemplated. In some examples, the secondary display communication interface 176 is a networking port on the CP that enables the CP 104 to communicate with the secondary display unit 152 over a WAN, LAN, or other network, including the Internet.

The CP 104 includes three hard buttons: a "home" button 335 for returning the CP to a home screen for the device, a "quick off" button 340 for quickly deactivating stimulation, and a "reset" button 345 for rebooting the CP 104. The CP 104 also includes an "ON/OFF" switch 350, which is part of the power generation and management block (discussed below). In some embodiments, the "reset" button 345 may be eliminated, and the "ON/OFF" switch 350 can be used to remove all power when held long enough.

In FIG. 2, the CP 104 includes the primary display screen 168 arranged for viewing by the clinician operating the CP 104 and configured to display information relating to the programmer 104, the IPG 102, the secondary display unit 152, the PFT 210, and/or the surgeon input device 212. The input mechanism 170 permits a user to control images on the display and to make selections within a limited scope, so as to control the relationships between different control aspects. In FIG. 3, the primary display screen 168 and the input mechanism 170 are merged into a touch screen I/O device 375 for providing a user interface with the clinician. The touch screen display 375 can be a liquid crystal display (LCD) having a resistive, capacitive, or similar touch-screen technology. It is envisioned that multitouch capabilities can be used with the touch screen display 375 depending on the type of technology used. However, in place of a touch screen display, a computer keyboard, a standard pointing device, such as a mouse or trackball, or other input devices are also contemplated.

The CP 104 includes a camera 380 allowing the device to take pictures or video. The resulting image files can be used to document a procedure or an aspect of the procedure. For example, the camera 380 can be used to take pictures of barcodes associated with the IPG 102 or the leads 120, or documenting an aspect of the procedure, such as the positioning of the leads. Similarly, it is envisioned that the CP 104 can communicate with a fluoroscope or similar device to provide further documentation of the procedure. Other devices can be coupled to the CP 104 to provide further information, such as scanners or RFID detection. Similarly, the CP 104 includes an audio portion 385 having an audio codec circuit, audio power amplifier, and related speaker for providing audio communication to the user, such as the clinician or the surgeon.

The CP 104 further includes a power generation and management block 390. The power block 390 has a power source (e.g., a lithium-ion battery) and a power supply for providing multiple power voltages to the processor, LCD touch screen, and peripherals.

In one embodiment, the CP 104 is a handheld computing tablet with touch screen capabilities. The tablet is a portable personal computer with a touch screen, which is typically the primary input device. However, an external keyboard or mouse can be attached to the CP 104. The tablet allows for mobile functionality not associated with even typical laptop personal computers.

In operation, the IPG 102 (which may also be an EPG) through the use of the implanted medical electrical leads 108, and specifically the electrodes 110 (FIG. 1B), stimulates neurons of the spinal cord 10. The IPG 102 selects an electrode stimulating configuration, selects a stimulation waveform, regulates the amplitude of the electrical stimulation, controls the width and frequency of electrical pulses, and selects cathodic or anodic stimulation. This is accomplished by a healthcare professional (e.g., a clinician), using the CP 104, setting the parameters of the IPG 102. The setting of parameters of the IPG results in a "program," which is also referred to herein as a "protocol," for the electrode stimulation. Programming may result in multiple protocols that the patient can choose from. Multiple protocols allow, for example, the patient to find a best setting for paresthesia at a particular time of treatment.

Returning now to the block diagram in FIG. 2, the secondary display unit 152 includes a relatively large display screen suitable for displaying system information to a surgeon or patient when used in the operating room, to a group of students, or to other groups. In one example, the secondary display unit 152 is disposed within an operating surgical room where it can be seen by a surgeon performing a surgery. The secondary display unit 152 includes a display screen 182, a speaker 184, a microphone 186, and a communication interface 188. It is understood that the speaker 184 and the microphone 186 are optional and may be omitted in some embodiments.

Because the CP 104 is a portable device and includes a relatively small primary display screen 168, it is not easily viewed by multiple people at a single time. However, the display screen 182 of the secondary display unit 152 is sized larger than the display screen 168 of the primary CP 104 and enables multiple people to simultaneously view the screen and allows surgeons to see the IPG status or action taken by the CP. In one example, the display screen 182 is more than twice the size of the primary display screen 168 of the CP 104. One exemplary display screen 182 is sized with a diagonal measurement greater than about 22 inches. Another exemplary display screen 182 is sized with a diagonal measurement greater than about 30 inches. Other sizes, both larger and smaller are contemplated. The display screen, in some examples, is a large monitor whose image is controlled entirely from the clinician programmer 104. In one example it is a smart monitor configured to convert information received from the clinician into a three-dimensional image and to display information in a three-dimensional manner.

The speaker 184 and microphone 186 are linked respectively with the microphone 174 and the speaker 172 on the CP 104. As such, communication is enabled between individuals proximate the secondary display unit 152 and the individual proximate to and operating the CP 104. As indicated above, this may be useful when the CP 104 and the secondary display unit 152 are in different locations. In one embodiment, the communication via the microphones and the speakers on the CP 104 and the secondary display unit 152 communicate over the same secondary display communication interface 176 and the CP interface 190. In other embodiments, they have separate communication channels, wired or wireless, for transmitting and receiving information.

The communication interface 188 in the secondary display unit 152 includes a CP interface 190 and a peripheral interface 192. The CP interface 190 is configured, depending on the embodiment, to receive data or signals from the secondary display communication interface 176 on the CP 104. For example, the CP interface 190 may connect to the secondary display communication interface 176 on the CP 104 via HDMI using a Type D Micro to Type A HDMI connector. Alternatively, or in addition to, the HDMI signals may be compatible with DVI. Thus, the CP 104 can also be connected, with the proper cabling, to other external display devices that only support DVI input.

In one example, the secondary display unit is configured to display the same information as the primary display screen 168 on the CP 104. This mirroring of the screens 168, 182 enables a surgeon in an operating room and the clinician who is operating the CP to see the same information, albeit in different locations.

The peripheral interface 192 is configured, depending on the embodiment, to receive data or signals from the IPG 102, the PFT 210, and the surgeon input device 212. In one example, the peripheral interface 192 comprises a MICS RF transceiver used to communicate with the IPG 102, the PFT 210, and the surgeon input device 212. As described above, the MICS RF transceiver may utilize a loop antenna for its communications, with other antennas, such as, for example, dipole, chip antennas, or others known in the art also considered. For example, a communications link can be established between the IPG 102 and the secondary display unit 152, and communications can then occur over a MICS transceiver using a standard frequency for a medical device transmission.

The IPG 102 includes all the treatment information required for treating the patient condition with the electrodes 110, but also includes a communication interface 192. In one embodiment, the communication interface 192 is configured to communicate with one or both of the CP 104 and the secondary display unit 152 and convey information including IPG status, treatment status, program operation, and other information to the CP 104 and/or the secondary display unit 152. The secondary display unit 152, under the control of the CP 104, may communicate with the IPG communication interface 192 and may convey new treatment programs, including electrode management routines, such as activating particular electrodes in a particular order with a particular intensity, by varying amplitude, pulse width, and frequency. Once these treatment programs are received, the IPG 102 may execute or respond to the received information as directed by the clinician programmer 104 through the secondary display unit 152. In one example, the IPG 102 also communicates directly with the peripheral communication interface 178 of the CP 104. This embodiment may work well when the IPG 102 is in the proximity of the CP 104 and able to receive information via wireless or wired transmission.

The PFT 210 is sized to be held by a patient and can be used to provide feedback during programming of the IPG 102. In one example, the PFT 210 may be used to provide feedback to the CP 104 while a clinician operating the CP 104, under instruction from the surgeon, develops the protocol for the IPG 102. In one example, the PFT 210 is an ergonomic handheld device having a sensor (also referred to as input), a controller, and a communications output. The sensor can include a discrete switch and/or a continuously variable input, such as through the use of a thermocouple, strain gauge, pressure sensor, piezoelectric device, accelerometer, displacement mechanism, or other variable sensing mechanism. It is envisioned that the use of a continuously variable input can provide magnitude information, thereby providing improved feedback information from the patient.

The PFT 210 includes a communication interface 214 that communicates information to the communication interface 188 on the secondary display unit 152, which relays the information to the CP 104. For example, the communication interface 214 and the peripheral interface 192 may establish a communication link. Communications can then occur over Bluetooth or other wireless formats. The CP 104 may then, if appropriate, adjust the display imagery on one or both of the primary display screen 168 and the display screen 182 of the secondary display unit 152 to reflect the patient feedback.

The PFT 210 is used to help the surgeon program the IPG 102 based on patient feedback. For example in use, the CP 104 activates one or more of the electrodes (on leads that are connected to the IPG 102) in various patterns. When the patient feels a sensation as a result of a stimulus, such as a stimulus for paresthesia, he or she activates a sensor on the PFT 210. The activation of the sensor indicates to the clinician programming system 150 that the patient felt the stimulus and can also convey the degree of sensation that is felt, depending on the type of sensor that is employed. Given that there may be a delay from the time the patient feels a sensation and activates the sensor, the system 150 then re-stimulates the most recently-activated combinations of electrodes, and the patient again uses the PFT 210 to indicate when (and to what degree) a sensation is felt in order to determine the combination of electrodes to which the patient was reacting. Further description of methods for use of the PFT 210 are disclosed in U.S. patent application Ser. No. 13/118,781, filed on May 31, 2011, titled "Device to Provide Feedback For Neurostimulation Programming", the contents of which are incorporated herein by reference in its entirety.

Figure 4:
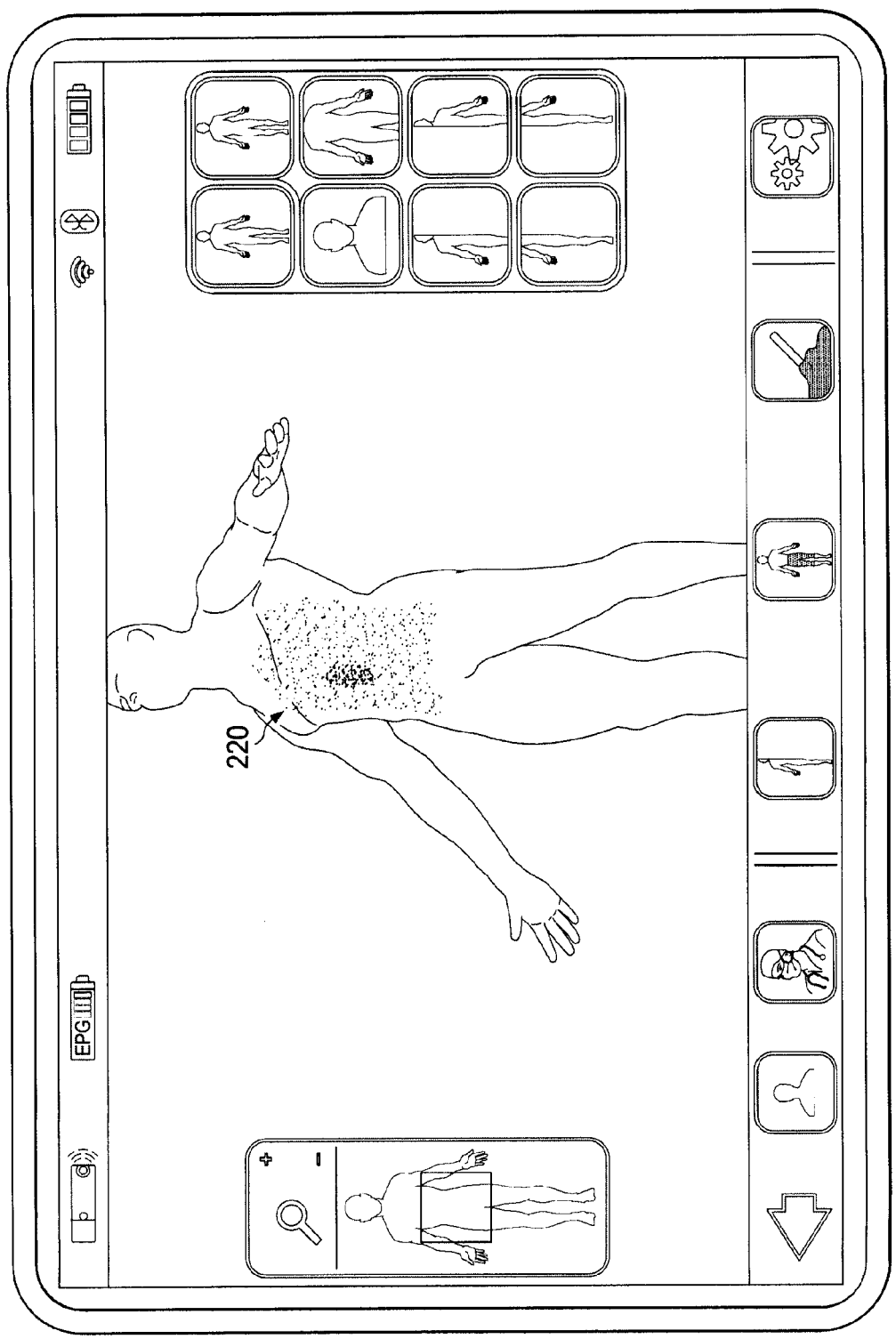
FIG. 4 is an exemplary user interface illustrating the generation of a pain map or a stimulation map.

In some embodiments, the patient may use the clinician programmer or another portable device (for example an electronic tablet or an electronic programmer) to draw a pain map and/or a stimulation map. For example, referring to FIG. 4, an exemplary user interface 215 illustrating the generation of a pain map or a stimulation map 220 is illustrated. The user interface 215 may be displayed through a touch-sensitive screen. The user interface 215 shows a three-dimensional model of a human body, which can be rotated and moved around. Using his fingers, the patient may be able to paint the pain/stimulation map 220 on a region of the human body to indicate the sensation he is experiencing in that region. During the painting process, the patient may choose the hue and the intensity of the color of the painted pain and stimulation regions to represent the various types of pain/stimulation or degrees of pain/stimulation. It is understood that the pain/stimulation map 220 may also be generated by a healthcare professional. The PFT 210 may be used to indicate the intensity of pain/stimulation, but the maps are displayed either on the clinician programmer (or tablet) or the external monitor.

Referring back to FIG. 2, the surgeon input device 212 is sized and configured to be held by the surgeon or other medical care provider within the sterile field in an operating room. Using it, the surgeon can control one or both of the CP 104 and the secondary display unit 152. The surgeon input device 212 may permit a surgeon to select particular images on the display screen 182 of the secondary display unit 152, which may be conveyed to the CP 104. In one embodiment, the CP allows a surgeon to select a particular electrode from an array of electrodes and to select activation including increasing and decreasing amplitude and frequency. This communication to the CP 104 through the secondary display unit 152 may help reduce the reliance on verbal cues and instructions passed to the clinician outside the sterile field, allowing the clinician to rely on more visual instructions simultaneously viewable by both the surgeon and the programming clinician. The surgeon input device 212 includes a communication interface 216 that communicates information to the communication interface 188 on the secondary display unit 152, which relays the information to the CP 104. For example, the communication interface 216 and the peripheral interface 192 may establish a communication link, and communications can then occur over a MICS transceiver using a standard frequency for a medical device transmission. The CP 104 may then, if appropriate, adjust the display imagery on one or both of the primary display screen 168 and the display screen 182 of the secondary display unit 152 to reflect the surgeon input.

In one aspect, this disclosure is directed to a method for displaying information on a CP to operating room staff working within a sterile field. One example of this will be described with reference to FIG. 5. The CP 104 is not a sterile device, so the external connection of the secondary display communication interface 176 may be used to display content shown on the primary display screen 168 of the CP 104 to those in the operating room while the CP 104 remains outside of the sterile field and outside the operating room. Making the content of the primary display screen 168 of the CP 104 viewable by the physician performing a procedure reduces the interaction required between a physician and the individual outside of the sterile field assisting the physician by performing the programming on the CP 104. The physician can easily see the operating state of the IPG 102 as shown on the CP 104 and does not require the individual assisting outside of the sterile field to describe it. Allowing the physician himself to see the actual information on the primary display screen 168 of the CP 104 reduces the time spent to perform the procedure, as well as reduce the occurrence of any miscommunications and any resulting undesirable consequences, for example reducing the probability of an infection.

Figure 5:
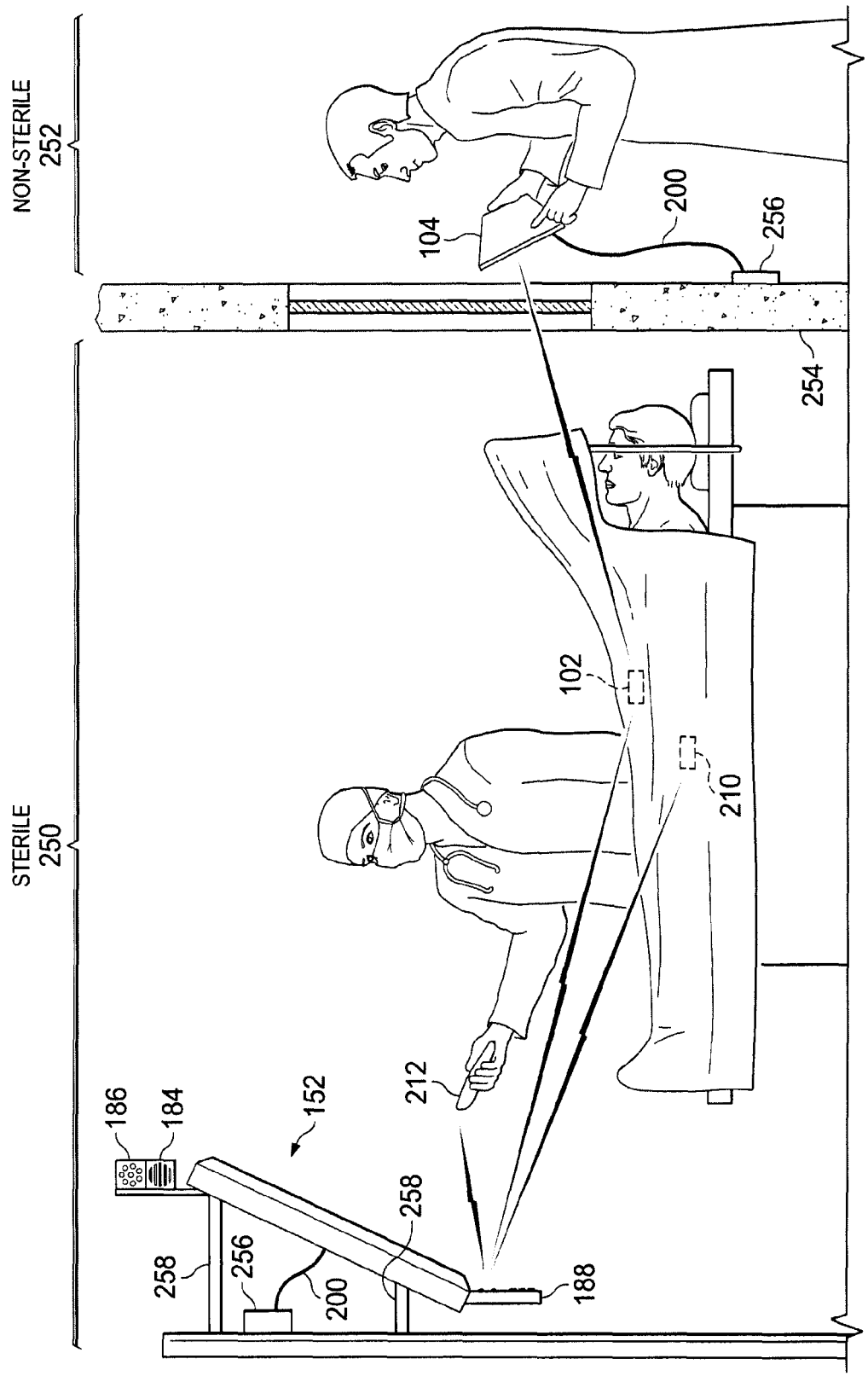
FIG. 5 is an illustration of an exemplary use of the exemplary external monitor interface system of FIG. 2 in accordance with one exemplary aspect of the present disclosure.

FIG. 5 shows an operating room 250 and a clinician room 252. These are separated by a physical barrier, shown here as a wall structure 254. The operating room 250 is or includes a sterile field. In the example, shown a surgeon performs a procedure on a patient having an implanted IPG 102, and a clinician stands in the clinician room 252 operating the CP 104. The patient holds the PFT 210, and the surgeon holds the surgeon input device 212. In this example, the CP 104 is disposed in the clinician room 252, and the secondary display unit 152 and the IPG 102 are disposed in the surgical room 250. In this embodiment, the CP 104 is a tablet controller fitted with a suitable communications port, for example a micro-HDMI connector. The CP 104 is able to drive a signal over the secondary display communication interface 176 of the CP 104 and copy the display from the primary display screen 168 on the CP 104 to the external secondary display screen 182 on the secondary display unit 152.

The secondary display unit 152 is, in this example, hung on a wall of the surgical room in a fixed location visible to the surgeon and his operating staff. In other examples, it may be visible to the surgeon and his operating staff through a window or other barrier. As can be seen, the secondary display unit 152 is much larger than the CP 104 and is configured to be easily viewable by several people at the same time. In one example, the secondary display screen 182 is at least double the size of the primary display screen 168 of the CP 104. The secondary display unit 152 includes the speaker 184, the microphone 186, and the communication interface 188. Verbal instructions from the surgeon to the clinician are captured at the microphone 186 and emitted from the speaker 172 on the CP 104. Likewise, verbal responses from the programmer can be captured by the microphone 174 on the CP 104 and heard though the speaker 184. In some embodiments, the contents of the screen of the CP 104 may also be broadcast via a suitable communications network.

In the example shown, the secondary display unit 152 is hung via a fixation structure 258. Here, the fixation structure 258 is a fixation bracket that extends from a rigid structure, such as the wall, and supports the secondary display unit 152 in a fixed position. As can be seen, the secondary display unit 152 is tipped at an angle to promote simple and convenient viewing from the sterile field in the surgical room. In this example it is spaced from the surgical area, and may not be a sterile device itself It is operated without tactile feedback or input directly on the secondary display unit 152, and may be considered a hands-free device. It is controlled via the CP 104, but also may relay information collected from the IPG 102, the PFT 210, and the surgeon input device 212. Information is also relayed back from the secondary input to the CP display.

The communication interface 188 on the secondary display unit 152, and particularly the peripheral interface 192 communicates with one or more of the IPG 102, the PFT 210, and the surgeon input device 212. As indicated above, in one embodiment, the peripheral interface 192 provides two-way communication to each of these devices. In other examples, the peripheral interface 192 receives one-way communication from one or more of these devices. The communication interface 188 may be attached onto or otherwise carried on the display screen 182 or on or within its housing.

In the illustrated embodiment, a cable 200 extends from the secondary display communication interface 176 of the CP 104 to an outlet 256 shown on the wall structure 254. In this example, the secondary display communication interface 176 of the CP 104 is a micro-HDMI connector, and the cable 200 may be an HDMI cable extending between the secondary display communication interface 176 of the CP 104 and outlet 256.

The outlet 254 connects to an outlet 256 in the surgical room 250 via a cable within the wall, from which a cable extends to the secondary display unit 152. Over this wired line, the CP 104 communicates display information for presentation on the secondary display unit 152. That is, the CP 104 is able to drive a HDMI signal over the secondary display communication interface 176 of the CP 104 to copy the content from the primary display screen 168 on the CP 104 to the external display screen 182 on the secondary display unit 152. This can also be done via wireless communication. In other words, the wire 200 may not be needed in some embodiments, as the communication between the secondary display unit 152 and external devices are done wirelessly. In that case, the secondary display unit 152 may only need a power source or a battery.

In one example, the displayed content mirrors the information displayed on the CP 104. Accordingly, by viewing the secondary display unit 152, the surgeon sees the same information as the clinician operating the CP 104. In another example, the displayed content is different than or includes additional information than that displayed on the CP 104. Accordingly, with this extended display feature, the surgeon, by viewing the secondary display unit 152, sees different, but relevant information than the clinician operating the CP 104.

In one example, the information shown on the CP 104 and/or the secondary display unit 152 includes IPG status information, charge information, program information, status and settings for one or more electrodes, including frequency, pulse width, and amplitude information for one or more electrodes. It may also include additional information. In one visualization of the patient's organs, x-ray information, or status of the patient's overall condition including items such as vital signs, including blood pressure, temperature, respiratory rates, heart beat, and/or other vitals.

In one example, the secondary display unit 152 is connected to a Digital Video Interface (DVI) connector on the CP 104 and the content of the primary display screen 168 was cloned, copied, or replicated onto the display screen 182 of the secondary display unit 152 via the DVI interface. In one example, the system 150 achieves 30 frames per second (FPS) when outputting the primary display screen content to an 800×600 display screen 182. This is representative of the CP 104 because the data stream format output by the CP 104 over the HDMI interface may be nearly identical to that output from the DVI interface on the EVK.

In one example, the CP 104 requires the user to enable the secondary display screen 182 by selecting a display mode for the external display monitor 152. In one embodiment, the hardware for the secondary display communication interface 176 is arranged to detect when the external secondary display unit 152 is plugged in or otherwise connected. Using this functionality, the CP 104 may detect when the secondary display unit 152 is connected to the secondary display communication interface 176 of the CP 104, the driver in the CP 104 automatically switches to extending the display on the external monitor. Likewise, when the external secondary display unit 152 is detached, the CP 104 may disable the mirroring or extended display function.

Software modules on CP 104 provide instructions for accomplishing particular tasks handled by the CP 104. In the embodiment described above, the software includes a secondary display unit control module that controls the image generated on the secondary display screen 182. In one example, the module enables a user to select between two operating modes. For example, a first mode or mirroring mode may control the secondary display screen 182 to show content mimicking that shown on the primary display screen 164. In this mode, the CP 104 may generate display signals for transmission to the secondary display unit 152 so that the primary and secondary display screens show the same content. A second mode or extended display mode of the secondary display unit may control the secondary display screen 182 to show content different than that shown on the primary display screen 164. In this mode, the CP 104 may generate display signals for transmission to the secondary display unit 152 so that the primary and secondary display screens show different content, although some content may still overlap.

The ability to output the primary display screen display to an external, and notably, larger, secondary display unit 152, such as a large screen monitor or projector, provides a decided advantage when it comes to communicating instructions to and receiving verbal responses from a clinician outside the sterile field, such as in another room. The external secondary display unit 152 makes it much easier for the surgeon and others to view what is happening.

Figure 6:
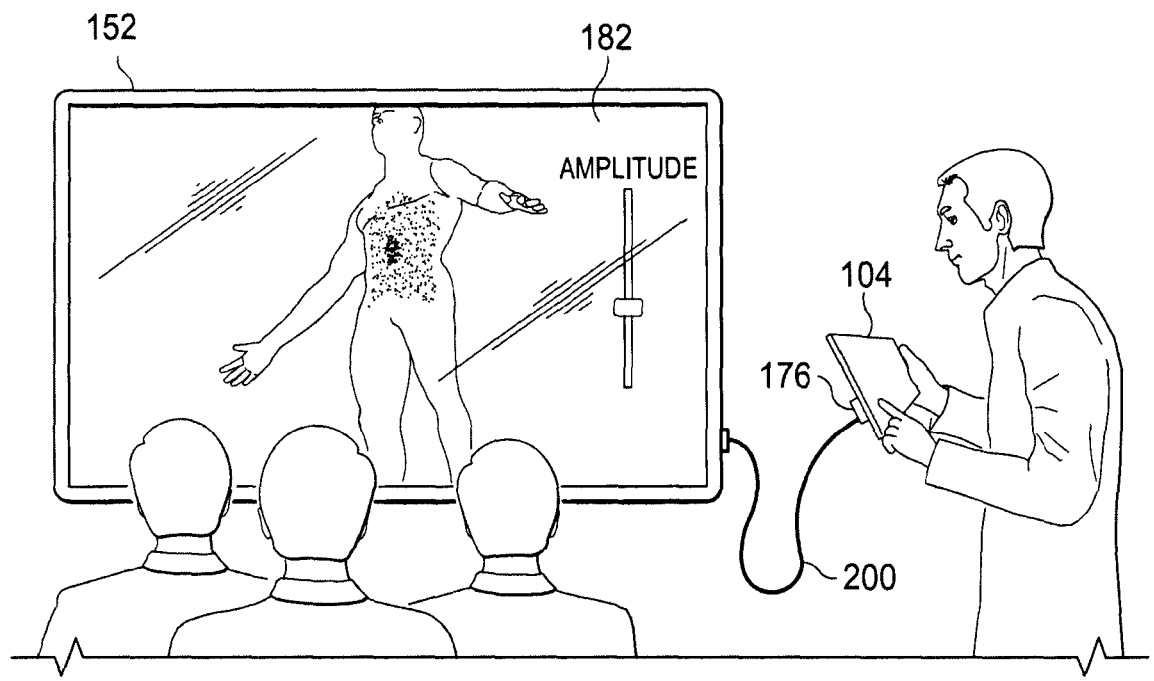
FIG. 6 is an illustration of an exemplary use of the exemplary external monitor interface system of FIG. 2 in accordance with one exemplary aspect of the present disclosure.

FIG. 6 shows another implementation of the system 150 according to one exemplary aspect of the present disclosure. In this example, the CP 104 and the secondary display unit 152 are illustrated being used to display an image to a number of individuals. The system illustrated may be used during instructional sessions, such as during training or education, for example.

In this embodiment, the CP 104 is a tablet controller fitted with a micro-HDMI connector, and the cable 200 is a HDMI cable extending between the secondary display communication interface 176 of the CP 104 and the communication interface 188 of the secondary display unit 152. The CP 104 is able to drive a HDMI signal over the secondary display communication interface 176 of the CP 104 and copies the display from the primary display screen 168 on the CP 104 to the external display screen 182 on the secondary display unit 152.

In this example, the display surfaces of the primary display screen 168 on the CP 104 and the external display screen 182 on the secondary display unit 152 are connected with DirectDraw. Using the DirectDraw API, a screen copy is made of the primary display screen 168 on the CP 104. A copy of the primarily display screen 168 is then drawn to the secondary display screen's surface. In one example, the contents displayed on the secondary display screen 182 mirrors that of the primary displace seen 168. The software routine adds the ability for the screen to be copied automatically at a user defined rate and for the copying to be enabled or disabled as necessary.

As discussed above, the CP 104 may require the user to enable the secondary display screen 182 by selecting a display mode for the external display monitor 152, may be arranged to detect when the external secondary display unit 152 is plugged in or otherwise connected. The ability to output the primary display screen display to an external, and notably, larger, secondary display unit 152, such as a large screen monitor or projector, provides a decided advantage when it comes to training personnel because it is much easier for multiple people to view what is happening.

In one embodiment, the surgeon input device 212 is not a handheld device, but is a motion detector associated with the secondary display unit 152. In this embodiment, the secondary display unit 152 may include a light source and a camera or sensor to generate a depth map or other imagery of the surgeon or other health care provider in the operating room 250. By detecting surgeon movement, the surgeon input device 212 may receive inputs for controlling either the CP or features of the secondary input monitor 152. For example, a surgeon may be able to select a particular electrode or an array of electrodes using the motion detector and increase or decrease the amplitude and frequency of pulses from the electrode or electrode array to create a treatment program that may be loaded onto the IPG 102.

Figure 7:
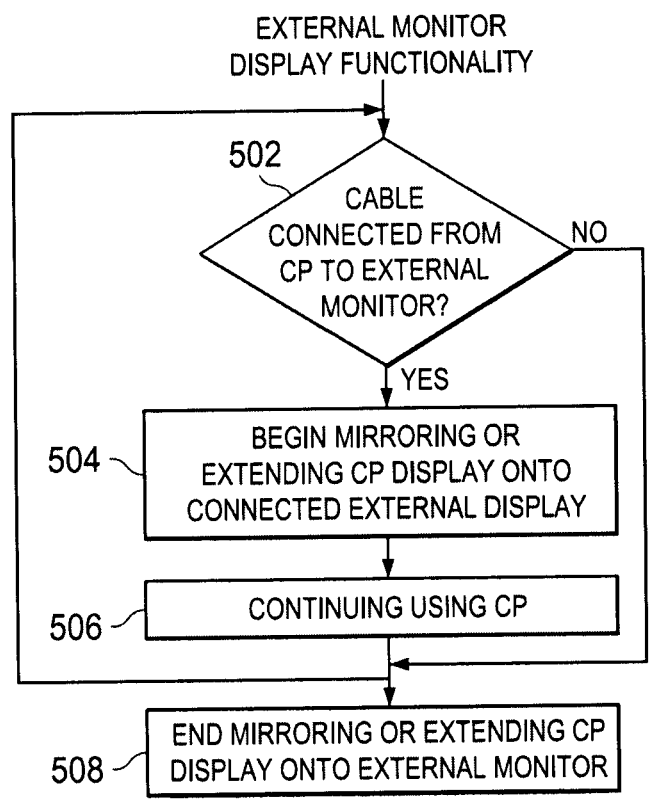
FIG. 7 is a flow chart showing an exemplary method of using the external monitor interface system of FIG. 2 in accordance with one exemplary aspect of the present disclosure.

FIG. 7 shows one method of activating the display functionality on the CP 104. The method includes querying whether the cable is connected for the CP to an external monitor, such as the secondary display unit 152, as indicated at step 502. If it is, then the CP 104 operates using control functionality that mirrors or extends the primary display screen 168 of the CP 104 onto the connected display screen 182 of the external display monitor 152, as indicated at a step 504. At a step 506, the CP may be used to program the IPG 102 in the manner known in the art. Meanwhile the secondary display unit 152 continues to mirror or extend the display serene. This continues until the system determines at step 502 that the cable 200 is not connecting the CP 104 and the secondary display unit 152. If not connected, the CP is operates to end mirroring or extending CP display onto the secondary display unit 152. So long as the CP 104 is connected, the functionality of the secondary display unit 152 may be utilized. For example, in embodiments using the PFT 210 and/or the surgeon input device 212, the CP 104 is configured so that all functionality is enabled when the CP 104 and the secondary display unit 152 are connected.

In use, a clinician may take the cable 200 and plug it into the secondary display communication interface 176 of the CP 104. With this connection made the CP 104 can send display information to the secondary display unit 152 for display on the display screen 182. In one embodiment, over the same cable 200, feedback information from the secondary display unit 152 can be transmitted to the CP 104. This feedback information may be from the secondary display unit 152, or relayed through the secondary display unit 152 to the CP 104 from the PFT 210, the IPG 102, or the surgeon input device 212. In addition, the audio feed between the speakers and microphones on the CP 104 and the secondary display unit 152 may also be carried over the cable 200. In other embodiments, the system 150 includes a separate feedback line and/or a separate audio feed line. In yet another embodiment, the communication occurs wirelessly over a direct connection, between the CP 104 and the secondary display unit 152, such as, for example, through infra-red transmission, or over an indirect connection, such as through a wireless network.

The IPG 102 may then be implanted using methods and techniques known in the art. The surgeon may give instructions to the programmer of the CP 104 to activate or deactivate particular electrodes to develop a treatment program that provides a suitable level of relief to the patient. Since the surgeon can see the secondary display unit 152, he knows whether his instructions are being properly carried out without additional questions or explanation from the programmer of the CP 104. This reduction in reliance on verbal instructions may increase efficiently of the surgical procedure. Further, during the procedure, the surgeon may intervene or request additional views of displayed information using the surgeon input device 212. This allows the surgeon to have a level of control over the CP 104, although that level of control may be a lesser level than the level of control of the programmer of the CP 104. In one example, the surgeon input device may allow the surgeon to select an electrode and modify its frequency or amplitude of applied stimulation. Although the patient programmer is not sterile, the surgeon input deice may be a sterile device, and in one embodiment, is a single-use device that is discarded after use.

During the programming process, information from the PFT 210 may be transmitted to the secondary display unit 152. The secondary display unit 152 may then relay the received information to the CP 104 for consideration or processing. Based on the patient feedback, the CP 104 may be controlled to update the images on the screens 164, 182 or provide additional information for programming the implant. Software on the CP 104 may control the images shown on the secondary display screen 182, as described above.

When a stimulation program is set, it may be transmitted to the IPG 102 either directly from the CP 104 or it may be transmitted to the secondary display unit for relay to the IPG 102. The IPG may then store the treatment program for operation.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A clinician programming system operable to control an implantable medical device, comprising:
  a clinician programmer with a housing, comprising:
    a processor and memory having executable instructions enabling programming of an implantable pulse generator;
    a user interface configured to receive inputs by a clinician instructing operation of an implantable pulse generator;
    a first display configured to display information indicative of the inputs by the clinician or display information indicative of status of an implantable pulse generator, the first display having a first display size;
    an implant communication interface configured to transmit information from the clinician programmer to an implantable pulse generator and configured to receive information from an implantable pulse generator; and
    a display communication interface configured to transmit content shown on the first display; and
    a microphone and a speaker; and
  a secondary unit separate from the housing of the clinician programmer, the secondary unit having a secondary microphone, a secondary speaker and a secondary display of a second display size larger than the first display size, the secondary display being configured to communicate with the clinician programmer via a secondary display communication interface, wherein the secondary display displays programming information of the implantable medical device substantially simultaneously as the programming information occurs on the first display of the clinician programmer and wherein the secondary microphone and secondary speaker are in electrical communication with the microphone and speaker of the clinician programmer.

2. The clinician programming system of claim 1, wherein the clinician programmer is a tablet style programmer and the display communication interface of the clinician programmer comprises a HDMI connector.

3. The clinician programming system of claim 1, further comprising an implantable pulse generator in communication with the implant communication interface of the clinician programmer.

4. The clinician programming system of claim 3, wherein the implant communication interface comprises a medical implant communication service (MICS) RF transceiver used to communicate with the implantable pulse generator.

5. The clinician programming system of claim 1, wherein the user interface is further configured to receive inputs selecting a stimulation program stored in the memory and operable on an implanted medical device.

6. The clinician programming system of claim 1, wherein the first display comprises a touch screen display, and wherein the user interface comprises a touch-sensitive graphical user interface that is implemented at least in part via the touch screen display.

7. The clinician programming system of claim 1, further comprising a patient feedback tool operable by a patient, the patient feedback tool being configured to communicate feedback information to the secondary unit, and the secondary unit being configured to communicate feedback information to the clinician programmer.

8. The clinician programming system of claim 1, further comprising a surgeon input device operable by a patient, the surgeon input device being configured to communicate feedback information to the secondary unit, and the secondary unit being configured to communicate feedback information to the clinician programmer.

9. The clinician programming system of claim 1, wherein the second display size is at least twice as large as the first display size of the clinician programmer.

10. The clinician programming system of claim 1, wherein the secondary microphone is configured to receive audio and transmit the audio to the clinician programmer.

11. The clinician programming system of claim 1, further comprising an HDMI cable connecting the display communication interface of the clinician programmer to the secondary unit to carry the information.

12. The clinician programming system of claim 1, wherein the display communication interface comprises an external display driver, the driver being operable via a selection at the user input to enable and disable the second display.

13. The clinician programming system of claim 1, wherein the secondary unit is mounted to a wall in a sterile operating room.

14. The clinician programming system of claim 1, wherein the secondary unit is configured to convert information received from the clinician programmer into a three-dimensional image.

15. The clinician programming system of claim 1, wherein the secondary unit is configured to mirror a content displayed on the first display of the clinician programmer but with enhanced resolution of the content.

16. The clinician programming system of claim 1, wherein the secondary display communication interface includes a DVI interface.

17. The clinician programming system of claim 1, wherein the processor of the clinician programmer is further configured to:
   detect whether a connection with the secondary unit exists;
   mirror the first display of the clinician programmer to the secondary display if the connection with the secondary unit exists; and
   disable the mirror of the first display if the connection with the secondary unit no longer exists.

18. A clinician programming system operable to control an implantable medical device, comprising:
   a clinician programmer with a housing, comprising:
      a processor and memory having executable instructions enabling programming of an implantable pulse generator;
      a user interface configured to receive inputs by a clinician instructing operation of an implantable pulse generator;
      a first display configured to display information indicative of the inputs by the clinician or display information indicative of status of an implantable pulse generator, the first display having a first display size;
      an implant communication interface configured to transmit information from the clinician programmer to an implantable pulse generator and configured to receive information from an implantable pulse generator; and
      a display communication interface configured to transmit content shown on the first display; and
      a microphone and a speaker; and
   a secondary unit separate from the housing of the clinician programmer, the secondary unit having a secondary microphone, a secondary speaker and a secondary display of a second display size larger than the first display size, the secondary display being configured to communicate with the clinician programmer via a secondary display communication interface and configured to display information received via the secondary display communication interface, wherein the secondary unit is mounted to a wall of a sterile room and wherein the secondary microphone and secondary speaker are in electrical communication with the microphone and speaker of the clinician programmer.

19. The clinician programming system of claim 18, wherein the clinician programmer is a tablet style programmer and the display communication interface of the clinician programmer comprises a HDMI connector.

20. The clinician programming system of claim 18, further comprising an implantable pulse generator in communication with the implant communication interface of the clinician programmer.

21. The clinician programming system of claim 20, wherein the implant communication interface comprises a medical implant communication service (MICS) RF transceiver used to communicate with the implantable pulse generator.

22. The clinician programming system of claim 18, wherein the user interface is further configured to receive inputs selecting a stimulation program stored in the memory and operable on an implanted medical device.

23. The clinician programming system of claim 18, wherein the first display comprises a touch screen display, and wherein the user interface comprises a touch-sensitive graphical user interface that is implemented at least in part via the touch screen display.

24. The clinician programming system of claim 18, further comprising a patient feedback tool operable by a patient, the patient feedback tool being configured to communicate feedback information to the secondary unit, and the secondary unit being configured to communicate feedback information to the clinician programmer.

25. The clinician programming system of claim 18, further comprising a surgeon input device operable by a patient, the surgeon input device being configured to communicate feedback information to the secondary unit, and the secondary unit being configured to communicate feedback information to the clinician programmer.

26. The clinician programming system of claim 18, wherein the second display size is at least twice as large as the first display size of the clinician programmer.

27. The clinician programming system of claim 18, wherein the secondary microphone is configured to receive audio and transmit the audio to the clinician programmer.

28. The clinician programming system of claim 18, further comprising an HDMI cable connecting the display communication interface of the clinician programmer to the secondary unit to carry the information.

29. The clinician programming system of claim 18, wherein information displayed on the secondary display is the same as information displayed on the primary display.

30. The clinician programming system of claim 18, wherein information displayed on the secondary display relates to programming information for an implantable pulse generator, but is different than information displayed on the primary display.

31. The clinician programming system of claim 18, wherein the display communication interface comprises an external display driver, the driver being operable via a selection at the user input to enable and disable the second display.

32. The clinician programming system of claim 18, wherein content shown on the secondary display mirrors content shown on the first display simultaneously.

33. The clinician programming system of claim 18, wherein the secondary unit is configured to convert information received from the clinician programmer into a three-dimensional image.

34. The clinician programming system of claim 18, wherein the secondary unit is configured to mirror a content displayed on the first display of the clinician programmer but with enhanced resolution of the content.

35. The clinician programming system of claim 18, wherein the secondary display communication interface includes a DVI interface.

36. The clinician programming system of claim 18, wherein the processor of the clinician programmer is further configured to:
- detect whether a connection with the secondary unit exists;
- mirror the first display of the clinician programmer to the secondary display if the connection with the secondary unit exists; and
- disable the mirror of the first display if the connection with the secondary unit no longer exists.

37. A clinician programming system operable to control an implantable medical device, comprising:
- a clinician programmer with a housing, comprising:
  - a processor and memory having executable instructions enabling programming of an implantable pulse generator;
  - a user interface configured to receive inputs by a clinician instructing operation of an implantable pulse generator;
  - a first display configured to display information indicative of the inputs by the clinician or display information indicative of status of an implantable pulse generator, the first display having a first display size;
  - an implant communication interface configured to transmit information from the clinician programmer to an implantable pulse generator and configured to receive information from an implantable pulse generator; and
  - a display communication interface configured to transmit content shown on the first display; and
  - a microphone and a speaker; and
- a secondary unit separate from the housing of the clinician programmer, the secondary unit having a secondary microphone, a secondary speaker and a secondary display of a second display size larger than the first display size, the secondary display being configured to communicate with the clinician programmer via a Digital Video Interface (DVI) connector and configured to display information received via the DVI connector and wherein the secondary microphone and secondary speaker are in electrical communication with the microphone and speaker of the clinician programmer.

38. The clinician programming system of claim 37, wherein the secondary unit is attached to a structure in a sterile operating room while the clinician programmer is disposed in a non-sterile room.

39. The clinician programming system of claim 37, wherein the secondary unit is configured to convert information received from the clinician programmer into a three-dimensional image.

40. The clinician programming system of claim 37, wherein the secondary unit is configured to mirror a content displayed on the first display of the clinician programmer in real time and with enhanced resolution of the content.

41. The clinician programming system of claim 37, wherein the processor of the clinician programmer is further configured to:
- detect whether a connection with the secondary unit exists;
- mirror the first display of the clinician programmer to the secondary display if the connection with the secondary unit exists; and
- disable the mirror of the first display if the connection with the secondary unit no longer exists.

* * * * *